United States Patent
Marczyk et al.

(10) Patent No.: US 9,241,709 B2
(45) Date of Patent: Jan. 26, 2016

(54) BARBED SUTURES

(75) Inventors: Stanislaw Marczyk, Stratford, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 601 days.

(21) Appl. No.: 13/149,077

(22) Filed: May 31, 2011

(65) Prior Publication Data

US 2012/0310278 A1 Dec. 6, 2012

(51) Int. Cl.
*A61B 17/04* (2006.01)
*A61B 17/06* (2006.01)
*A61B 17/00* (2006.01)

(52) U.S. Cl.
CPC . *A61B 17/06166* (2013.01); *A61B 2017/00526* (2013.01); *A61B 2017/06176* (2013.01)

(58) Field of Classification Search
CPC .............. A61B 17/06166; A61B 2017/00526; A61B 2017/06176
USPC .......................................... 606/151, 219, 228
See application file for complete search history.

(56) References Cited

U.S. PATENT DOCUMENTS

| | | | |
|---|---|---|---|
| 3,494,006 A * | 2/1970 | Brumlik | 24/447 |
| 3,981,051 A * | 9/1976 | Brumlik | 24/447 |
| 6,848,152 B2 | 2/2005 | Genova et al. | |
| 7,225,512 B2 | 6/2007 | Genova et al. | |
| 7,850,894 B2 | 12/2010 | Lindh, Sr. et al. | |
| 7,913,365 B2 | 3/2011 | Genova et al. | |
| 2002/0077661 A1 | 6/2002 | Saadat | |
| 2003/0041426 A1 | 3/2003 | Genova et al. | |
| 2004/0010275 A1 | 1/2004 | Jacobs et al. | |
| 2004/0039415 A1 | 2/2004 | Zamierowski | |
| 2004/0059378 A1 * | 3/2004 | Peterson et al. | 606/219 |
| 2004/0060409 A1 | 4/2004 | Leung et al. | |
| 2004/0060410 A1 | 4/2004 | Leung et al. | |
| 2004/0226427 A1 | 11/2004 | Trull et al. | |
| 2004/0237736 A1 | 12/2004 | Genova et al. | |
| 2005/0234480 A1 | 10/2005 | Nam et al. | |
| 2005/0234510 A1 * | 10/2005 | Zamierowski | 606/215 |
| 2007/0065663 A1 | 3/2007 | Trull et al. | |
| 2007/0187861 A1 | 8/2007 | Genova et al. | |

(Continued)

FOREIGN PATENT DOCUMENTS

DE 10 2007 058256 A1 5/2009
WO WO 2005/079388 A2 9/2005

(Continued)

OTHER PUBLICATIONS

European Search Report for EP 10177651.6-1526 date of completion is Dec. 14, 2010 (3 pages).

(Continued)

*Primary Examiner* — Alexander Orkin

(57) ABSTRACT

A system and method for affixing barbs on a suture are provided. In one embodiment, the system includes a suture supply mechanism for selectively retaining a length of suture and a barb supply mechanism for operably engaging a barb supply assembly including at least one barb. At least one of the suture supply mechanism and the barb supply mechanism are configured to approximate towards the other of the barb supply mechanism and suture supply mechanism to engage the at least one barb of the barb supply assembly with the suture of the suture supply assembly. Also provided are a barb for use in forming a barbed suture and a suture including at least one barb.

13 Claims, 14 Drawing Sheets

(56) References Cited

U.S. PATENT DOCUMENTS

| | | |
|---|---|---|
| 2007/0257395 A1 | 11/2007 | Lindh |
| 2008/0195147 A1 | 8/2008 | Stopek |
| 2008/0221618 A1 | 9/2008 | Chen et al. |
| 2008/0281357 A1 | 11/2008 | Sung |
| 2008/0312688 A1 | 12/2008 | Nawrocki |
| 2009/0076543 A1 | 3/2009 | Maiorino et al. |
| 2009/0248066 A1 | 10/2009 | Wilkie |
| 2009/0248071 A1* | 10/2009 | Saint et al. ............. 606/232 |
| 2009/0287245 A1 | 11/2009 | Ostrovsky et al. |
| 2010/0084780 A1 | 4/2010 | Lindh, Sr. |
| 2010/0137679 A1 | 6/2010 | Lashinski et al. |
| 2010/0146770 A1 | 6/2010 | Morency et al. |
| 2010/0275750 A1 | 11/2010 | Maiorino et al. |
| 2010/0313729 A1 | 12/2010 | Genova et al. |
| 2011/0046669 A1 | 2/2011 | Goraltchouk |
| 2011/0251640 A1* | 10/2011 | Lauria ..................... 606/228 |
| 2012/0116449 A1* | 5/2012 | Kirsch et al. ............. 606/228 |

FOREIGN PATENT DOCUMENTS

| | | |
|---|---|---|
| WO | WO2007/131019 A2 | 11/2007 |
| WO | WO 2008/042992 A2 | 4/2008 |
| WO | WO2008/141034 A1 | 11/2008 |
| WO | WO2008/157142 A2 | 12/2008 |
| WO | WO 2009/105663 A2 | 8/2009 |
| WO | WO 2009/129251 A2 | 10/2009 |
| WO | WO 2009/132284 A2 | 10/2009 |

OTHER PUBLICATIONS

European Search Report for EP 11250457.6-1269 date of completion is Jul. 19, 2011 (3 pages).

European Search Report for EP 12169370.9-1269 date of completion is Sep. 5, 2012 (8 pages).

European Search Report EP 12 16 5912 dated Jul. 18, 2012.

\* cited by examiner

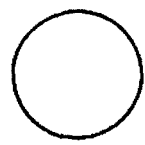  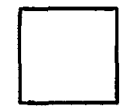
FIG. 2A  FIG. 2B  FIG. 2C
 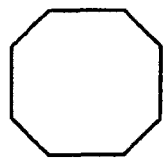 
FIG. 2D  FIG. 2E  FIG. 2F
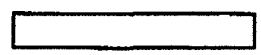
FIG. 2G

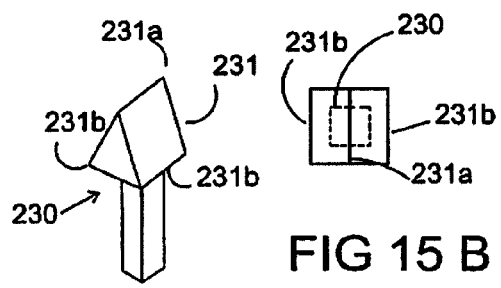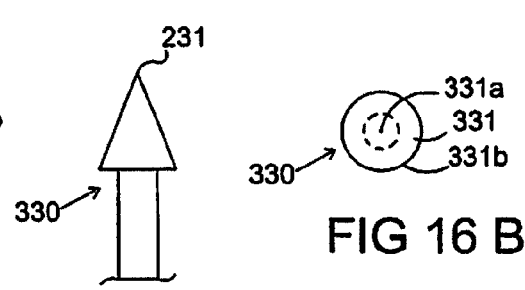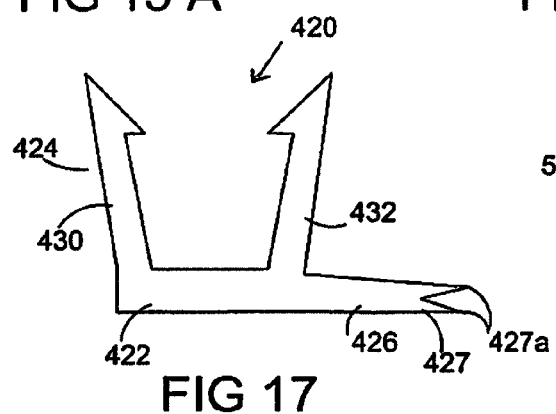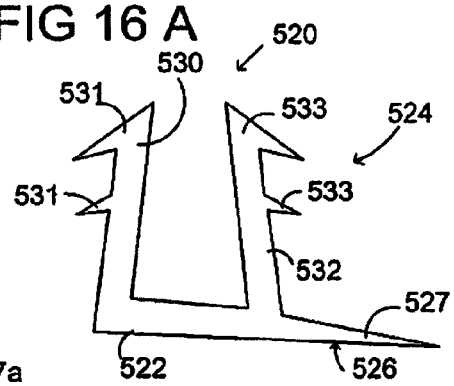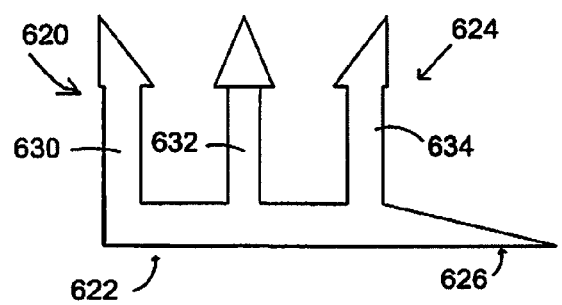

BARBED SUTURES

BACKGROUND

1. Technical Field

The present disclosure relates to barbed sutures and systems and methods for forming thereof. More particularly, the present disclosure relates to barbed sutures and systems and methods for affixing barbs on the suture.

2. Background of Related Art

Barbed sutures are generally made of the same materials as conventional sutures and offer several advantages for closing wounds compared with conventional sutures. A barbed suture includes an elongate body that has one or more spaced barbs that project from the surface of the elongate body along the length of the suture. The barbs are arranged to allow passage of the barbed suture in one direction through tissue but resist movement of the barbed suture in the opposite direction. Thus, one advantage of barbed sutures has been the provision of a non-slip attribute.

Barbed sutures are known for use in countless procedures. The number of barbs called for on a particular suture may be influenced by the type of tissue being sutured, the size of the wound and/or the strength required to hold the wound closed. Like a conventional suture, a barbed suture may be inserted into tissue using a surgical needle.

In some circumstances, a specific configuration of barbs on the exterior surface of the suture is preferred to achieve optimal wound closure holding for a particular wound. However, in other circumstances, where the wound or tissue repair needed is relatively small, a reduced number of barbs may be desired. In other circumstances, a two-way or bidirectional barbed suture is desirable where the barbs over a portion of the suture permit passing of the suture in one direction and barbs over another portion of the suture permit passing of the suture in a second direction to perform a tight closing stitch.

Various methods of forming barbs on sutures have been proposed. For example, barbs have been formed using mechanical cutting, laser cutting, injection molding, stamping, extrusion and the like. However, such methods may be difficult or costly to achieve the desired result with respect to getting the arrangement of barbs in a configuration needed for the appropriate procedure and for doing so in an efficient cost effective manner. These methods may also compromise the integrity of the suture as each relies on the suture for the material to create the barb.

Accordingly, there is a continuing need for a system and method of forming barbed sutures that is less difficult, more effective and/or economical. There is also a continuing need for methods which are able to vary the size, the number, the location and/or the depth of the barbs. It would further be beneficial if the barb is not formed from the material making up the suture.

SUMMARY

A system and method for affixing barbs on a suture are provided. In one embodiment, the system includes a suture supply mechanism for selectively retaining a length of suture and a barb supply mechanism for operably engaging a barb supply assembly including at least one barb. At least one of the suture supply mechanism and the barb supply mechanism are configured to approximate towards the other of the barb supply mechanism and suture supply mechanism to engage the at least one barb of the barb supply assembly with the suture of the suture supply assembly. The suture supply mechanism may include an anvil assembly for supporting a length of suture thereagainst. The anvil assembly may include an anvil for supporting the length of suture. The suture supply mechanism may be configured to advance a suture relative to the anvil assembly. The suture supply mechanism may include a suture supply assembly for supplying a length of a suture and a suture uptake assembly for taking up a length of the suture. The barb supply mechanism may include a pusher assembly for engaging the at least one barb of the barb supply assembly. The pusher assembly may include a pusher for engaging the at least one barb of the barb supply assembly. The barb supply mechanism may be configured to advance the barb supply assembly relative to the pusher assembly. Additionally, or in the alternative, the barb supply mechanism includes a sprocket for advancing the barb supply assembly relative to the pusher assembly.

Also provided is a barb configured for attachment to a suture. The barb includes a base portion, a retaining portion extending in a first direction from the base portion and configured for securing engagement with a suture, and a barb portion extending in a second direction from the base portion and configured for engaging tissue. The retaining portion may include one or more leg members. The one or more leg members may include at least a first anchor member. The first anchor member may include one or more barbs or ridgea. The first leg member may include a plurality of anchor members. The plurality of anchor members may alternate along the one or more leg members. The barb portion may include a pointed, rounded or arcuate elongate portion. Additionally provided is a suture including at least one of the above described barbs.

A barbed suture is also provided. The barb suture includes an elongate body including a multifilament structure and at least one barb including a retaining portion securely affixed within the multifilament structure. The retaining portion includes one or more leg members. The one or more leg members may include at least a first anchor member. The first anchor member may include one or more barbs or ridges. The one or more leg member may include a plurality of anchor members. The plurality of anchor members may be spaced along the one or more leg members. Additionally, or in the alternative, the plurality of anchor members may alternate along the one or more leg members. In one embodiment, the multifilament structure is braided.

Also provided is a barbed suture. The barbed suture includes an elongate body and at least one barb. The at least one barb includes a base portion, a retaining portion and a barb portion. The retaining portion securely affixes the at least one barb to the elongate body. The elongate body may comprise a monofilament or multifilament structure.

Additionally provided is a method of affixing a barb to a suture. The method includes the steps of providing a barb supply assembly including at least one barb having a retaining portion, aligning a suture with the retaining portion of the at least one barb, and advancing at least one of the suture and barb towards the other of the barb and suture such that the retaining portion of the barb engages the suture. The retaining portion may include at least one leg member. The leg member may include at least one anchor member for securing the barb to the suture. The suture may be multifilament.

BRIEF DESCRIPTION OF THE DRAWINGS

Various embodiments of the present disclosure will be described herein below with reference to the figures wherein:

FIGS. 2A-2G are ends views of sutures having alternative cross-sectional geometries, including circular (FIG. 2A), elliptical (FIG. 2B), square (FIG. 2C), star-shaped (FIG. 2D), octagonal (FIG. 2E), rectangular (FIG. 2F), and planar (FIG. 2G);

FIG. 15A is a side view of a leg member of a barb according to another embodiment of the present disclosure;

FIG. 15B is an end view of the leg member of FIG. 15A;

FIG. 16A is a side view of a leg member of a barb according to yet another embodiment of the present disclosure;

FIG. 16B is an end view of the leg member of FIG. 16A;

FIG. 17 is a top view of a barb according to another embodiment of the present disclosure;

FIG. 18 is a top view of a barb according to yet another embodiment of the present disclosure; and FIG. 19 is a top view of a barb according to still another embodiment of the present disclosure.

DETAILED DESCRIPTION

Figure 1A:
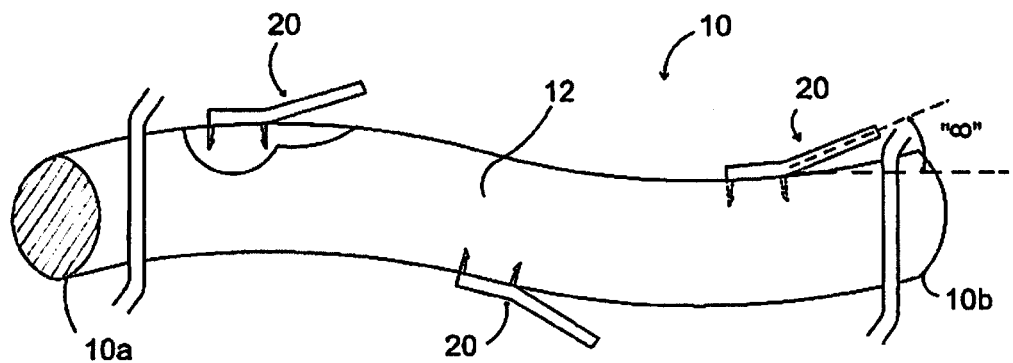
FIG. 1A is a perspective view of an embodiment of a barbed suture formed of a monofilament thread in accordance with the present disclosure.
Figure 1B:
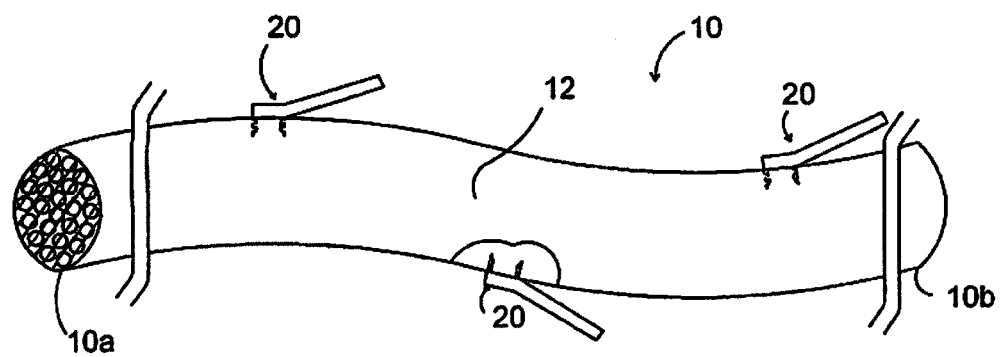
FIG. 1B is a perspective view of another embodiment of a barbed suture formed of a multifilament braided thread in accordance with the present disclosure.

Disclosed herein is a system and method for forming a barbed suture having at least one barb affixed along the length thereof. Referring now in detail to the drawings in which like reference numerals are applied to like elements in the various views, FIGS. 1A and 1B illustrate a length of suture 10 having an elongate body 12 and a plurality of barbs 20 affixed thereto. Suture 10 has a proximal end 10a and distal end 10b. Either or both of proximal and distal ends 10a, 10b may include a needle (not shown). As shown, barbs 20 are formed projecting outward from elongate body 12 of suture 10 in a first direction, however, it is envisioned that a first set of barbs 20 may project in a first direction along a first portion of elongate body 12 and a second set of barbs 20 may project in a second direction along a second portion of elongate body 12, thereby forming a two-way or bidirectional barbed suture. Barbs 20 form an angle "α" (FIG. 1A) of less than ninety degrees (90°) between barbs 20 and elongate body 12.

As shown in FIG. 1A, suture 10 is formed of a monofilament thread. With reference to FIG. 1B, as shown, suture 10 is formed of multifilament threads, e.g., a braided suture. As will become readily apparent from the following discussion, barbs 20 are particularly well suited for use with multifilament sutures. The braiding may be done by any method within the purview of those skilled in the art. Suture 10 may alternatively be formed of multifilament surgical fibers. The filaments and/or fibers used for forming suture 10 may be formed using any technique within the purview of those skilled in the art, such as, for example, extrusion or molding. In some embodiments, the suture may include a yarn made of more than one filament, which may contain multiple filaments of the same or different materials. Where suture 10 is made of multiple filaments, suture 10 may be made using any known technique such as, for example, braiding, weaving or knitting. The filaments may also be combined to produce a non-woven suture. The filaments themselves may be drawn, oriented, crinkled, twisted, commingled or air entangled to form yarns as part of the suture forming process.

Suture 10 may be formed of degradable materials, non-degradable materials, or combinations thereof. More particularly, suture 10 may be formed of a degradable material selected from the group consisting of polyesters, polyorthoesters, polymer drugs, polydroxybutyrates, proteins, carbonates, homopolymers thereof, copolymers thereof, and combinations thereof. In some embodiments, glycolide and lactide based polyesters, especially copolymers of glycolide and lactide, may be utilized to form suture 10.

Suitable non-degradable materials which may be utilized to form suture 10 include polyolefins, such as polyethylene and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. The polypropylene may be isotactic polypropylene or a mixture of isotactic and syndiotactic or atactic polypropylene.

As shown in FIGS. 1A and 1B, suture 10 is circular in cross-sectional geometry, however, the cross-sectional geometry of suture 10 may be of any suitable shape. For example, with reference to FIGS. 2A-2G, the cross-sectional geometry of suture 10 may include, circular (FIG. 2A), elliptical (FIG. 2B), square (FIG. 2C), star-shaped (FIG. 2D), octagonal (FIG. 2E), rectangular (FIG. 2F), and planar (FIG. 2G).

Figure 3:
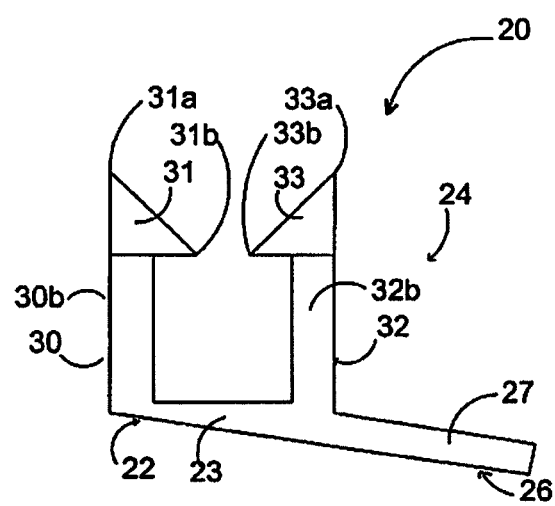
FIG. 3 is a top view of a barb according to an embodiment of the present disclosure.
Figure 4:
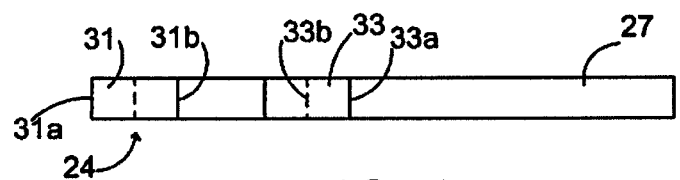
FIG. 4 is a front end view of the barb of FIG. 3.
Figure 5:
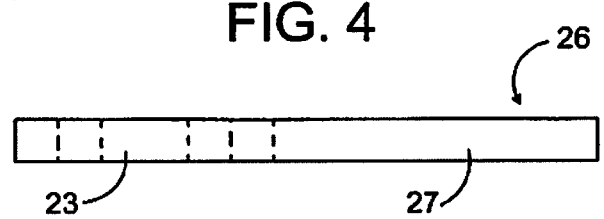
FIG. 5 is a back end view of the barb of FIGS. 3 and 4.

With reference to FIGS. 3-5, barb 20 is shown prior to attachment to elongate body 12 of suture 10. Barb 20 includes a base portion 22, a retaining portion 24 extending in a first direction from base portion 22, and a barb portion 26 extending in a second direction from base portion 22. Base portion 22, retaining portion 24 and barb portion 26 may be integrally formed or securely affixed to one another. Each of base portion 22, retaining portion 24 and barb portion 26 may be formed of the same or different material. The material forming base portion 22, retaining portion 24 and barb portion 26 may be the same and/or different from the material forming suture 10.

Still referring to FIGS. 3-5, base portion 22 includes a base member 23. Base member 23 may be tapered, as shown, or may include any other configuration suitable for facilitating passage through tissue as suture 10 is received through tissue. Retaining portion 24 includes a pair of leg members 30, 32 extending from base member 23 of base portion 22, however, in an alternative embodiment, retaining portion 24 may have only a single leg member, or may instead have three or more leg members. Leg members 30, 32 may be substantially similar in size and/or configuration, as shown, or may differ in size and/or configuration. Distal ends 30b, 32b of respective leg members 30, 32 each include an anchor member 31, 33.

Figure 3B:
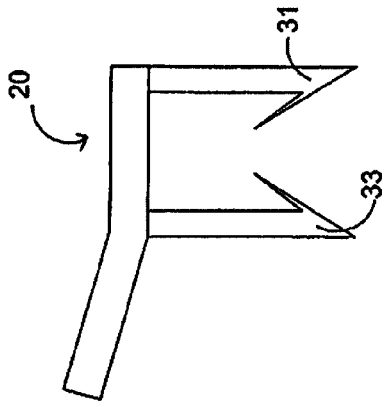
FIGS. 3A-3D are top views of barbs including anchor members according to alternative embodiments of the present disclosure, including inclined ridges (FIG. 3A), harpoons (FIG. 3B), barbs (FIG. 3C) and horizontal ridges (FIG. 3D)
Figure 3D:
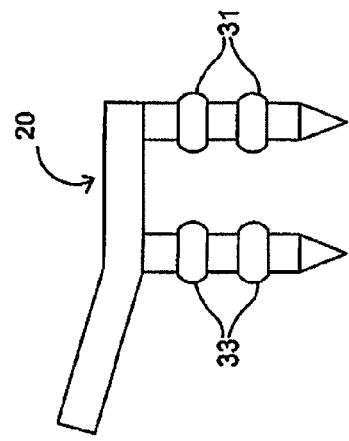
Figure 3A:
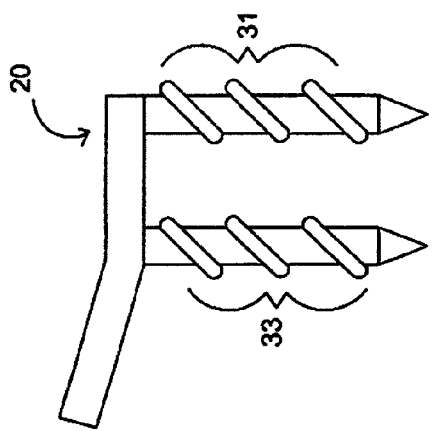
Figure 3C:
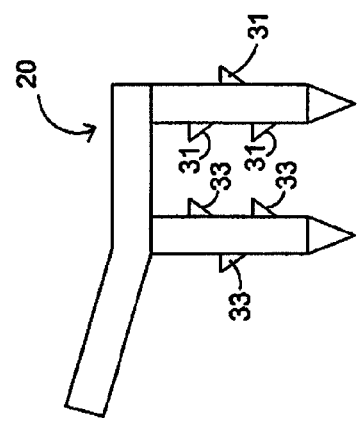

Anchor members 31, 33 each include a leading edge 31a, 33a and a trailing edge 31b, 33b. Leading edges 31a, 33a of anchor members 31, 33, respectively, are configured to facilitate penetration of leg members 30, 32 into elongate body 12 of suture 10. Trailing edges 31b, 33b of anchor members 31, 33, respectively, are configured to facilitate fixation of leg members 30, 32 to elongate body 12 of suture 10. As shown, anchor members 31, 33 form substantially hook-shaped members, however, alternatively shaped anchor members are envisioned, including, for example, inclined ridges (FIG. 3A), harpoons (FIG. 3B), barbs (FIG. 3C) and horizontal ridges (FIG. 3D). Although shown formed on distal ends 30b, 32b of leg members 30, 32, it is envisioned that one or more anchor members 31, 33 may be formed along the length of leg members 30, 32 (FIGS. 3A, 3C and 3D). Although described for use with monofilament and multifilament sutures, leg members 30, 32 and anchor members 31, 33 of barbs 20 are particularly well suited for reception between and retention with the threads of a multifilament suture.

Referring still to FIGS. 3-5, leg members 30, 32 and/or anchor members 31, 33 may include a coating (not shown) for facilitating the attachment and/or securement of barb 20 to elongate body 12 of suture 10. In one embodiment, leg members 30, 32 have a coating such as a lubricant for facilitating penetration of leg members 30, 32 into elongate body 12 of suture 10. The coating may also, or instead, include an adhesive for facilitating fixation of leg members 30, 32 or anchor members 31, 33, to elongate body 12 of suture 10. The adhesive may be activated by heat, light, chemicals, exposure to air or fluids, or any other known means. Alternatively, the adhesive may include a material that activates upon contact with suture 10.

Figure 6A:
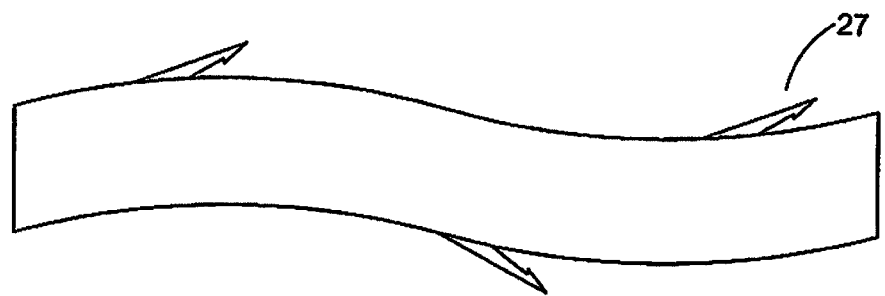
FIGS. 6A-6C are perspective views of a barbed suture including alternative embodiments of barb portions according to the present disclosure, including harpoon-shaped (FIG. 6A), rounded (FIG. 6B) and arcuate (FIG. 6C)
Figure 6B:
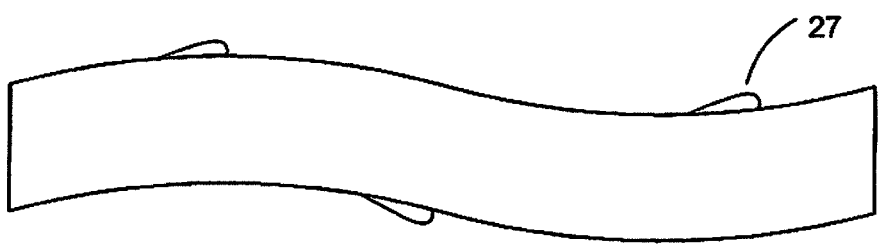
Figure 6C:
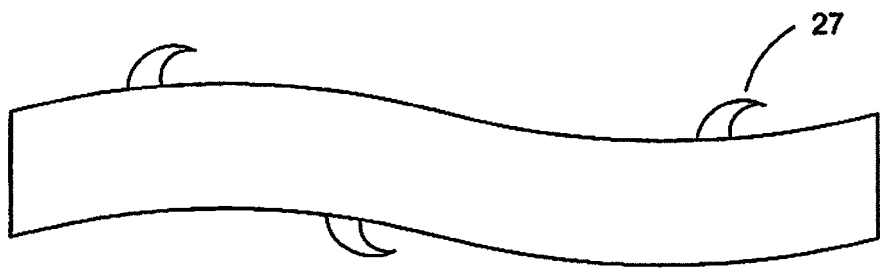
Figure 7:
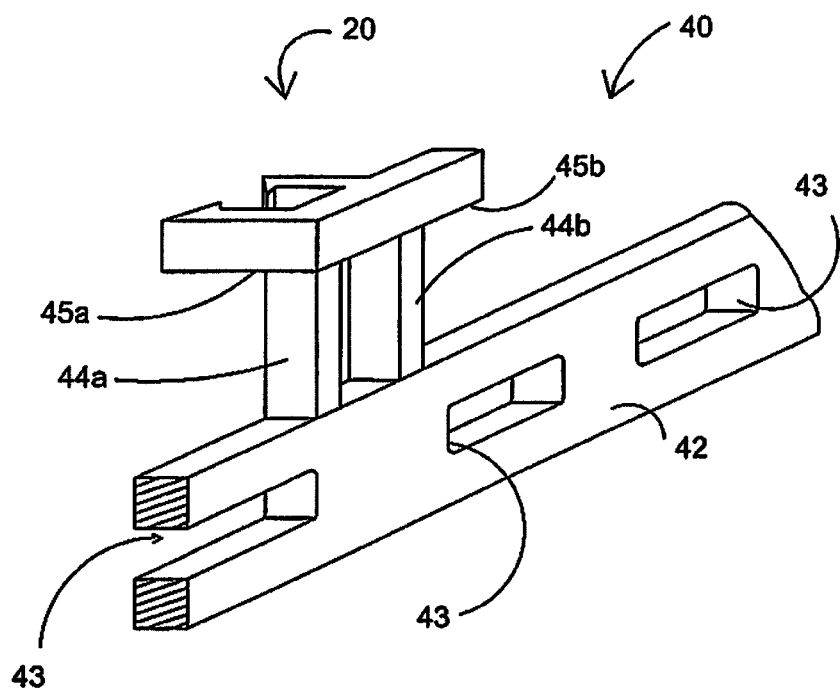
FIG. 7 is a perspective view of a section of an embodiment of barb supply assembly in accordance with the present disclosure.
Figure 8:
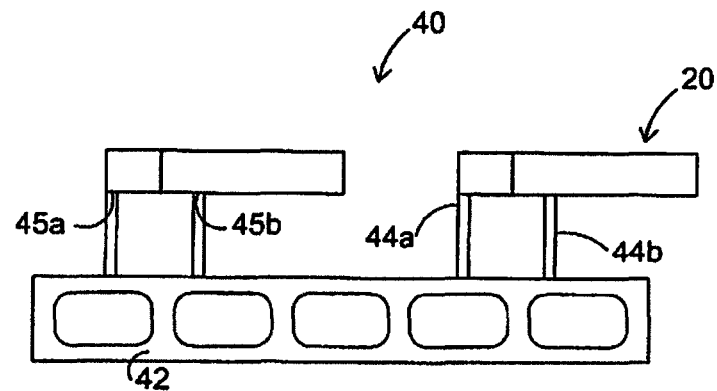
FIG. 8 is a front view of another section of the barb supply assembly of FIG. 7.
Figure 9:
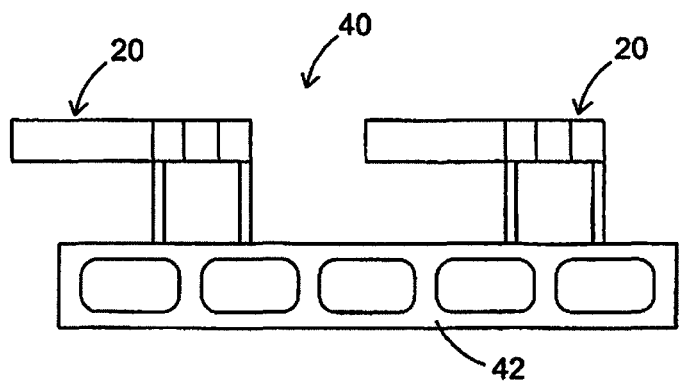
FIG. 9 is a back side view of the section of the barb supply assembly of FIG. 8.
Figure 10:
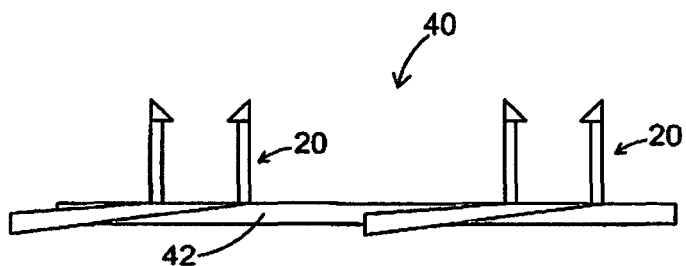
FIG. 10 is a top view of the barb supply assembly of FIGS. 8 and 9.

With reference still to FIGS. 3-5, barb portion 26 of barb 20 defines an elongate member 27. As shown, elongate member 27 is axially aligned with base portion 22 of barb 20. In an alternative embodiment, elongate member 27 is axially offset or extends at an angle with respect to base portion 22. Elongate member 27 may be substantially rectangular, as shown or may instead be pointed and/or tapered, e.g., harpoon-shaped (FIG. 6A), rounded (FIG. 6B), arcuate (FIG. 6C) or otherwise suitably configured for engaging tissue to prevent retraction of suture 10 through the tissue. When barb 20 is secured to suture 10 (FIG. 1A), barb portion 26 is configured to permit the passage of suture 10 through tissue in a first direction and to prevent passage of suture 10 through tissue in a second direction. Thus, once barb 20 is affixed to elongate body 12 of suture 10, barb portion 26 is configured to operate in a manner similar to a barb that is cut or otherwise formed directly on elongate body 12 of suture 10.

With reference now to FIGS. 7-10, an assembly for supplying a plurality of barbs 20 is shown generally as barb supply assembly 40. Supply assembly 40 includes a carrier strip 42 and a plurality of barbs 20. As shown, barbs 20 are secured to carrier strip 42 by support posts 44a, 44b. Alternatively, barbs 20 may be directly secured to carrier strip 42. As will be discussed in further detail below, support posts 44a, 44b are configured to align barbs 20 with elongate body 12 of suture 10 such that retaining portions 24 of barbs 20 may be affixed to elongate body 12. Barbs 20 may be secured to support posts 44a, 44b in any manner within the purview of one skilled in the art, including with adhesives, ultrasonic welding, mechanical fasteners or the like. Alternatively, carrier strip 42, support post 44a, 44b and barbs 20 may be integrally formed in a mold or otherwise, to form a single unit. Support posts 44a, 44b may include a perforation or indentation 45a, 45b providing a weakened portion for facilitating the separation of barb 20 from support posts 44a, 44b.

Figure 11:
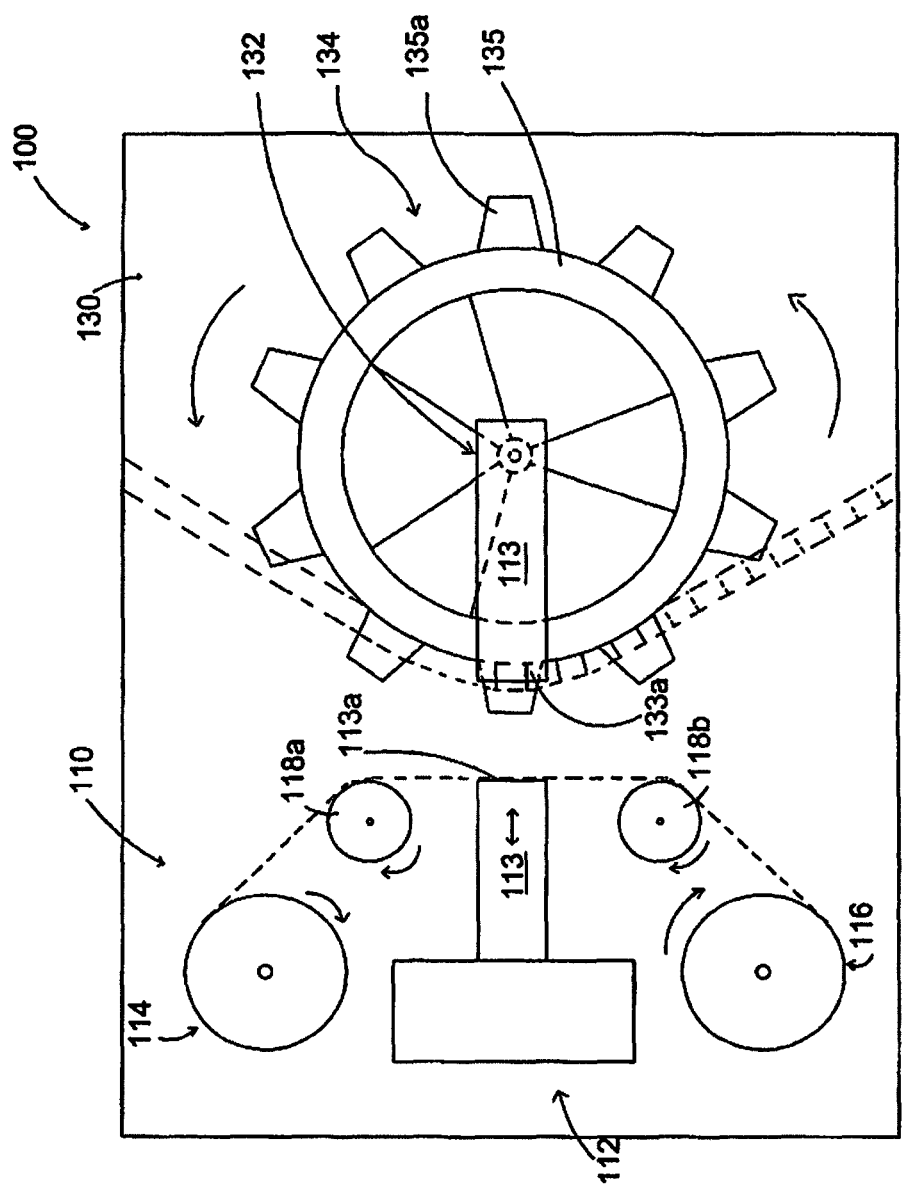
FIG. 11 is a top view of a barb fixation system according to an embodiment of the present disclosure.

Still referring to FIGS. 7-10, carrier strip 42 includes an elongated, substantially planar member defining a plurality of openings 43. Openings 43 are configured to be selectively engaged by a barb supply mechanism 130 (FIG. 11). Although shown including openings 43 for engagement by barb supply mechanism 130, it is envisioned that carrier strip 42 may be alternatively configured for engagement by barb supply mechanism 130. For example, carrier strip 42 may include slots and/or ridges in place of opening 43 to facilitate engagement of barb supply mechanism 130 with carrier 42.

With reference now to FIG. 11, a system for affixing one or more barbs 20 to elongate body 12 of suture 10 is shown generally as barb fixation system 100. Fixation system 100 includes a suture supply mechanism 110 and barb supply mechanism 130. Suture supply mechanism 110 includes an anvil assembly 112, a suture supply assembly 114, and a suture uptake assembly 116. Anvil assembly 112 includes an anvil 113 having a suture engagement surface 113a configured to support a length of suture 10. Suture engagement surface 113a may be flat, as shown, or may instead be contoured to correspond with a cross-sectional profile of suture 10 for more securely supporting a length of suture 10. As will be discussed in further detail below, anvil 113 may be configured for advancement and retraction relative to barb supply mechanism 130. Alternatively, or in addition, suture supply mechanism 110, in its entirety, may be configured for advancement and retraction relative to barb supply mechanism 130. Suture supply mechanism 110 may also be configured for such that anvil assembly 112 may be raised and/or lowered relative to barb supply mechanism 130 to align barb 20 with suture 10.

With reference still to FIG. 11, a pair of rollers 118a, 118b are configured to direct a length of suture 10 from suture supply assembly 114, across suture engagement surface 113a of anvil 113, to suture uptake assembly 116. In one embodiment, suture supply and uptake assemblies 114, 116 each include a spool for supplying and receiving suture 10, respectively. Although the following disclosure will relate to barb fixation system 100 including suture supply mechanism 110, the aspects of the present disclosure may be modified for use with other mechanisms capable of selectively supplying suture 10 to an anvil assembly.

Still referring to FIG. 11, barb supply mechanism 130 includes a pusher assembly 132 and an advancement assembly 134. Pusher assembly 132 includes a pusher 133 having a barb engagement portion 133a. Barb engagement portion 133a is configured to engage base portion 22 of barb 20 (FIG. 3). Barb engagement portion 133a may be flat, as show, or may instead be contoured to correspond with a cross-sectional profile of base portion 22 of barb 20. Pusher 133 may further include a knife (not shown) for separating barb 20 from support posts 44a, 44b of supply assembly 40. The knife may be heated, ultrasonic vibrated or otherwise manipulated to facilitate separation of barb 20 from support posts 44a, 44b and/or carrier strip 42. As will be discussed in further detail below, pusher assembly 132 and/or pusher 133 may be configured to advance and retract relative to suture supply mechanism 110. Alternatively, or in addition, barb supply mechanism 130, in its entirety, may be configured for advancement and retraction relative to suture supply mechanism 110.

With reference still to FIG. 11, advancement assembly 134 includes a sprocket 135. Sprocket 135 defines a substantially circular member including a plurality of teeth 135a extending radially outward therefrom. Teeth 135a are configured to be selectively received within openings 43 formed in carrier strip 42 of supply assembly 40 as sprocket 133 is rotated about its central axis. Either or both of pusher assembly 132 and advancement assembly 134 may be raised or lowered together or independently to adjust the distance between assemblies 132, 134 and to adjust the position of assemblies 132, 134 relative to anvil assembly 112 of suture supply assembly 110. Although the following disclosure will relate to barb fixation system 100 including barb supply mechanism 130, the aspects of the present disclosure may be modified for use with other mechanisms capable of selectively supplying barb 20 of barb assembly 40 relative to suture 10.

Figure 12:
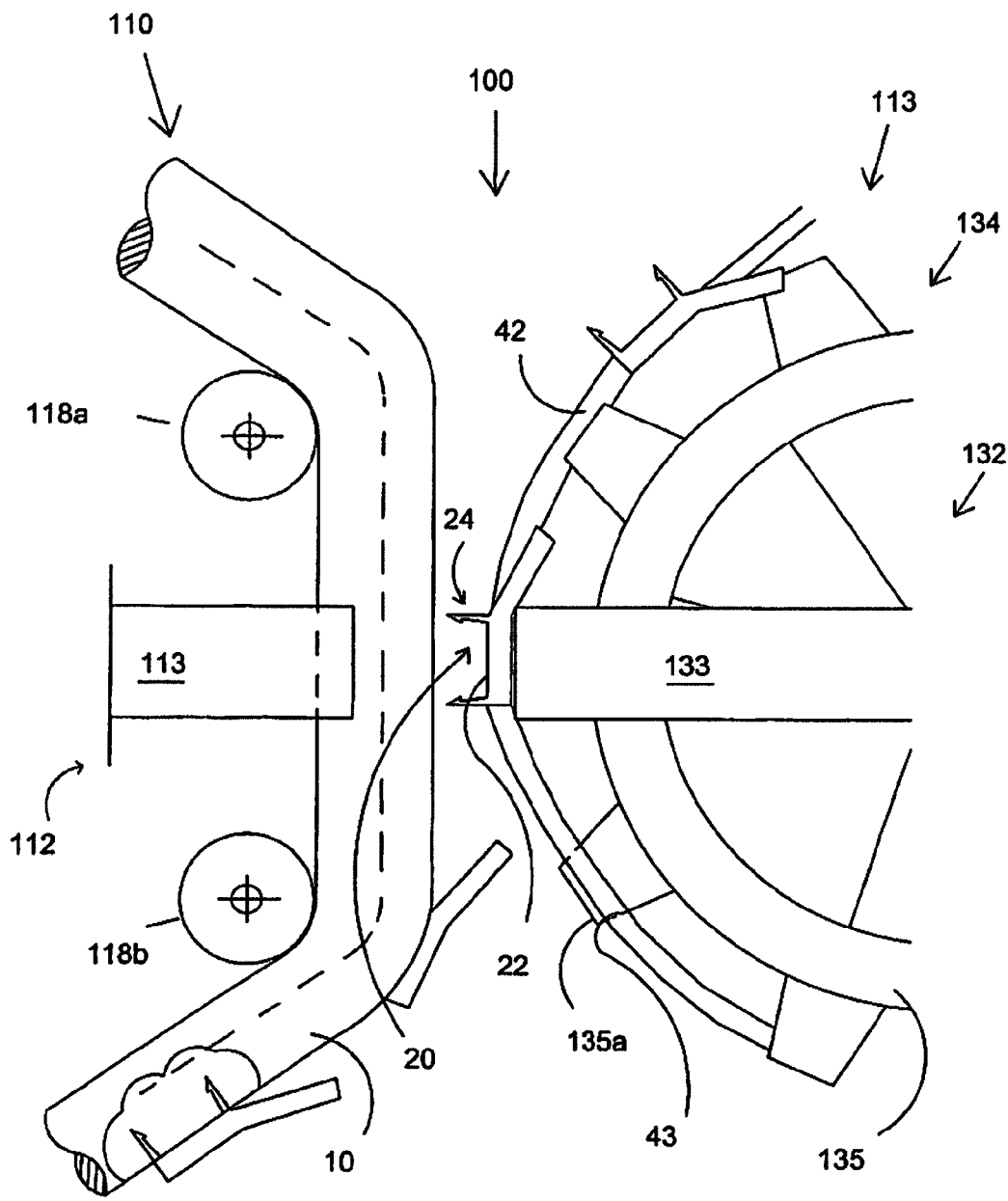
FIG. 12 is a top sectional view of the barb fixation system of FIG. 11, including a length of suture and a length of the barb supply assembly of FIGS. 7-9, in an initial or loaded condition.
Figure 13:
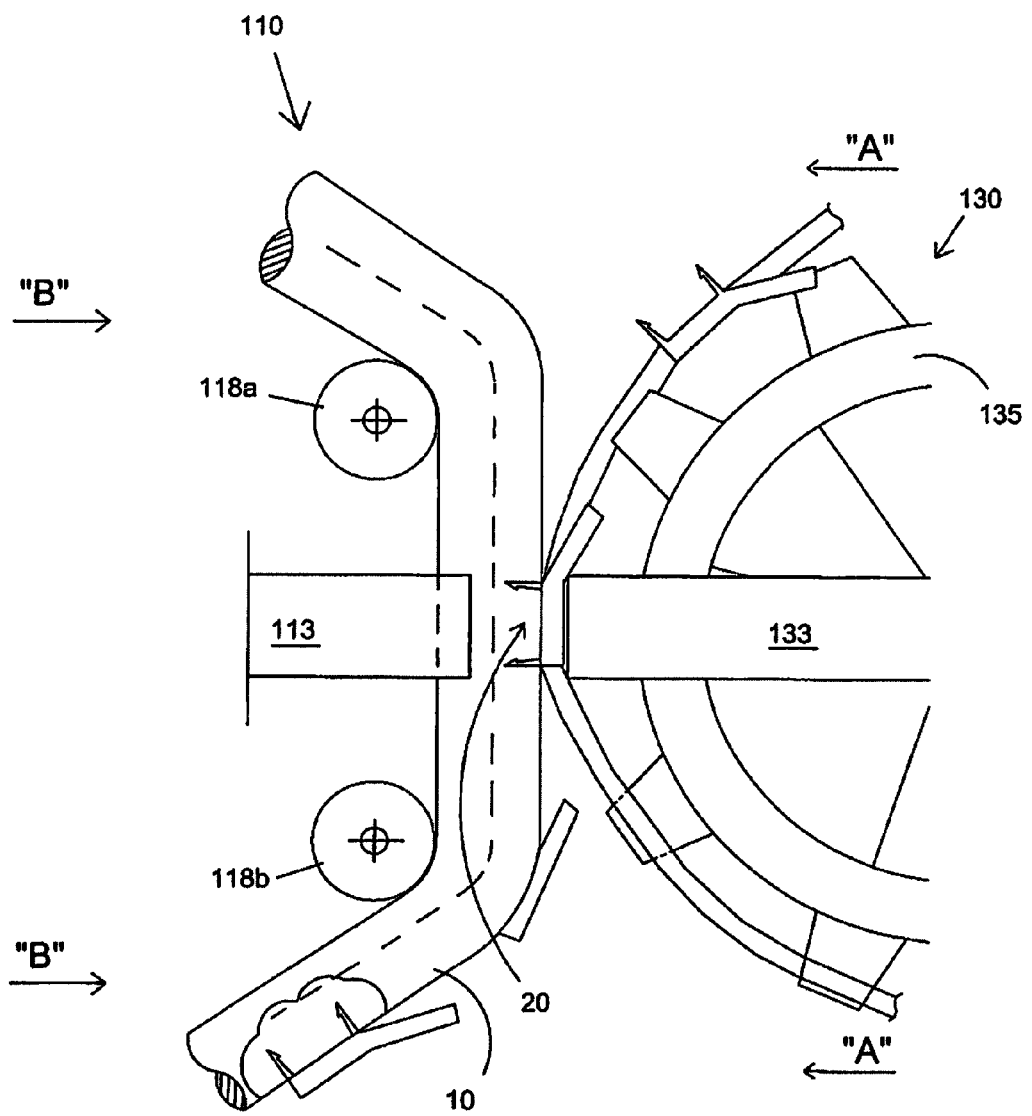
FIG. 13A is the top sectional view of FIG. 12 showing a first method of affixing a barb from the barb supply assembly with the suture.
FIG. 13B is the top sectional view of FIG. 12 showing a second method of affixing a barb from the barb supply assembly with the suture.
FIG. 13C is the top sectional view of FIG. 12 showing a third method of affixing a barb from the barb supply assembly with the suture.
Figure 13:
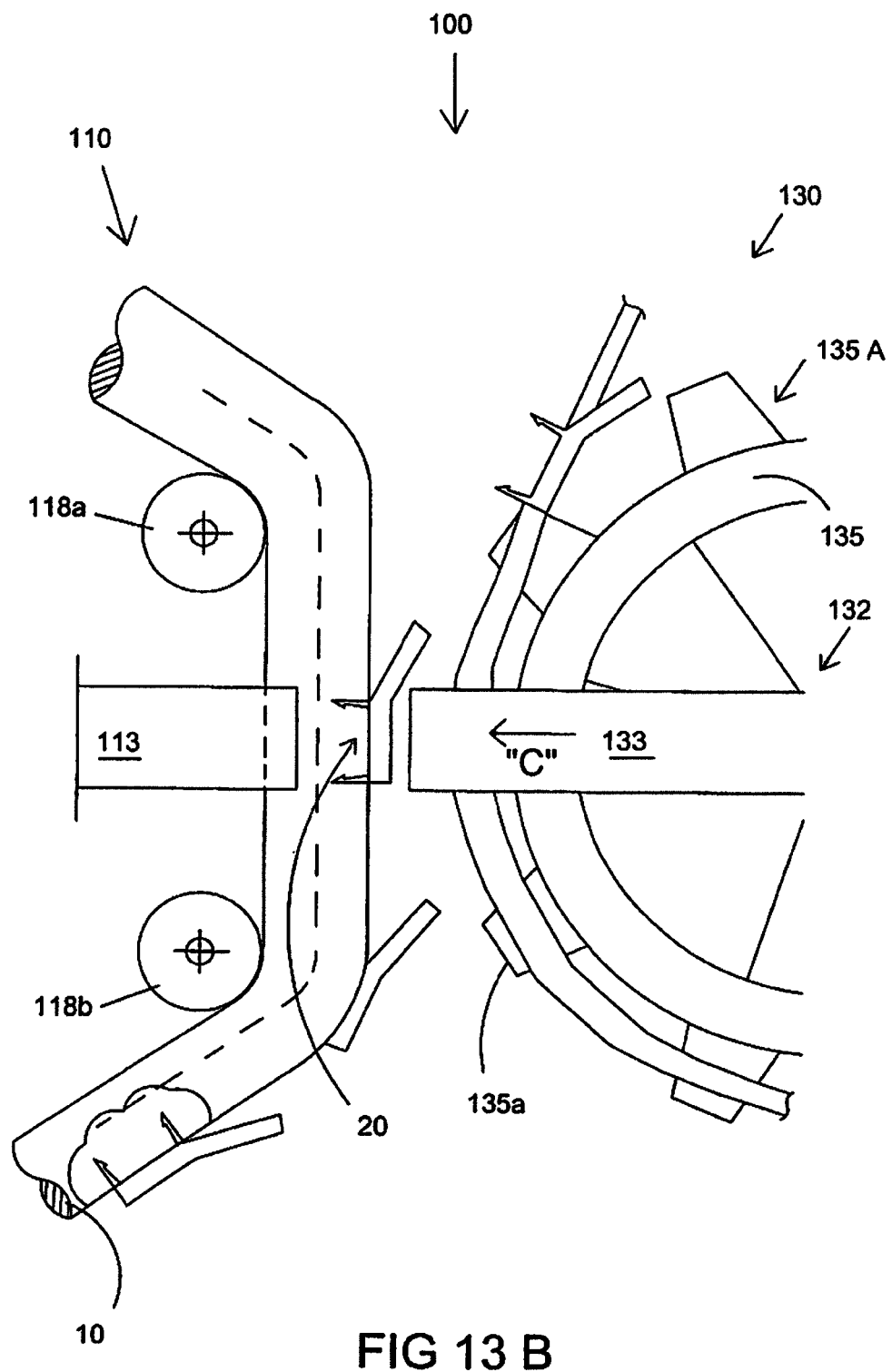
Figure 13:
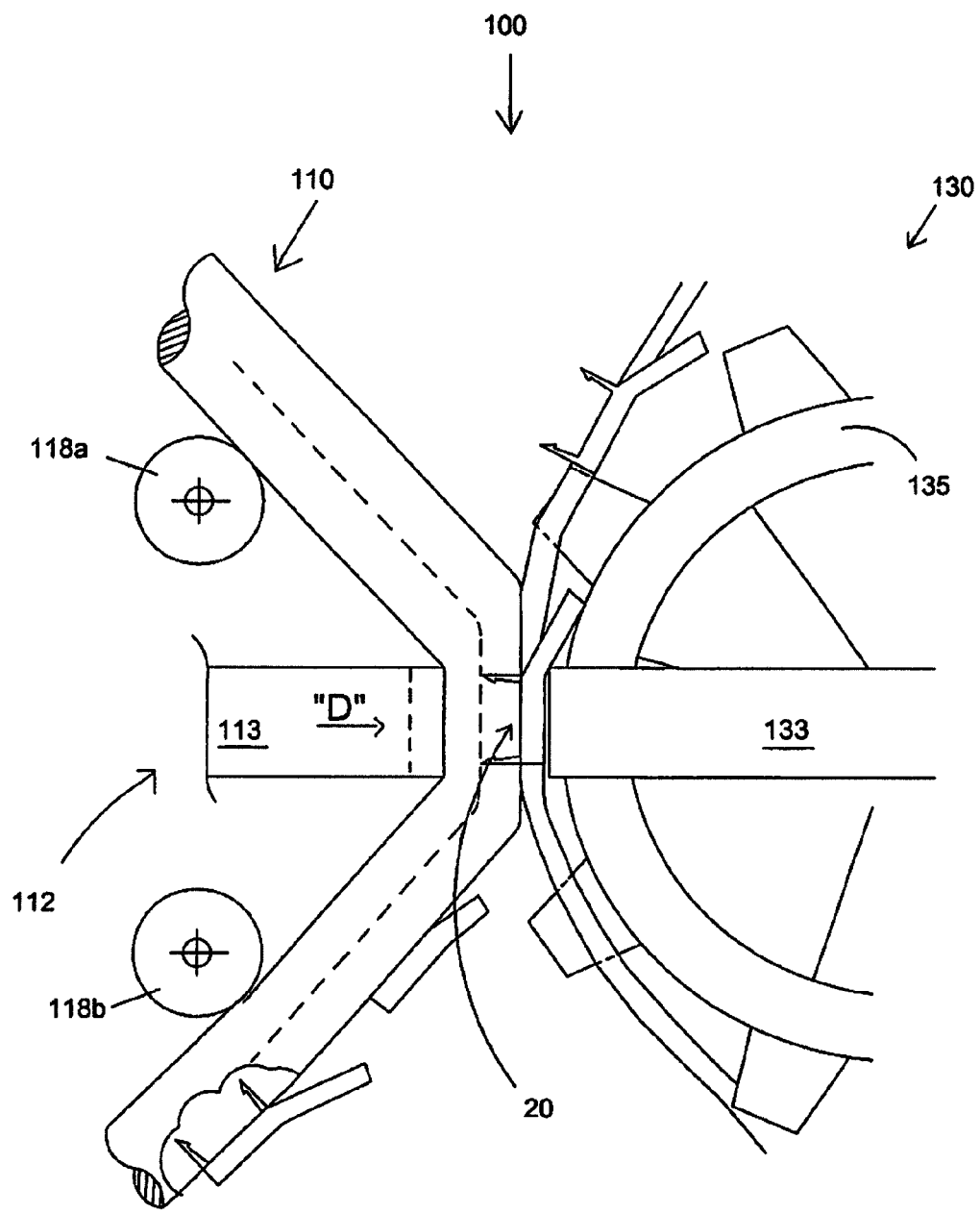

The use of barb fixation system 100 will now be described with reference to FIGS. 11-14. Referring initially to FIG. 12, suture supply mechanism 110 is loaded with a length of suture 10 to selectively position suture 10 relative to barb supply mechanism 130. Specifically, a length of suture 10, provided from suture supply assembly 114 (FIG. 11), is received about roller 118a, across suture engagement surface 113a of anvil 113, about roller 118b and onto suture uptake assembly 116. As discussed above, although shown including suture supply mechanism 110, barb fixation system 100 may include any mechanism capable of selectively moving and retaining suture 10 relative to an anvil.

Still referring to FIG. 12, barb supply assembly 40 is loaded onto barb supply mechanism 130. Specifically, teeth 135a of sprocket 135 are received within openings 43 of carrier strip 42 of barb supply assembly 40. Sprocket 135 is then rotated until a barb 20 of barb supply assembly 40 is aligned with anvil assembly 112 of suture supply assembly 110. Pusher assembly 132 and advancement assembly 134 may then be raised or lowered to adjust the distance therebetween in order to align pusher 133 of pusher assembly 132 with base portion 22 of barb 20. Pusher assembly 132 and advancement assembly 134 may also be raised or lowered relative to anvil assembly 112 to align retention portion 24 of barb 20 with elongate body 12 of suture 10. Alternatively, or in addition, suture supply assembly 110 may be raised or lowered to align suture 10 with retention portion 24 of barb 20. As discussed above, although shown including barb supply mechanism 130, barb fixation system 100 may include any mechanism capable of selectively moving barb supply assembly 40 relative to suture supply mechanism 110.

Reference now to FIGS. 13A-13C, once retaining portion 24 of barb 20 is aligned with suture 10, either or both of suture supply mechanism 110 and barb supply mechanism 130 may be activated to cause the approximation of either or both of barb 20 and suture 10 relative to the other of barb 20 and suture 10. With reference to FIG. 13A, in one embodiment, barb supply mechanism 130, in its entirety, is advanced relative to suture supply mechanism 110, as indicated by arrows "A", to cause the engagement of barb 20 with suture 10. Alternatively, suture supply mechanism 110, in its entirety, is advanced relative to barb supply mechanism 130, as indicated by arrows "B", to cause the engagement of barb 20 with suture 10. In another embodiment, both suture supply mechanism and barb supply mechanism, in their entirety, are advanced relative to each other to cause the engagement of barb 20 with suture 10. Turning to FIG. 13B, in another embodiment, pusher 133 of pusher assembly 132 is advanced relative to sprocket 135 of advancement assembly 134 and relative to anvil 113 of anvil assembly 112, as indicated by arrow "C", to cause the engagement of barb 20 with suture 10. Turning to FIG. 13C, in yet another embodiment, anvil 113 of anvil assembly 112 is advanced relative to barb supply mechanism 130, as indicated by arrow "D", to cause the engagement of barb 20 with suture 10.

As discussed above, the engagement of barb 20 with suture 10 may be achieved using multiple methods. Regardless of which method is selected to cause the engagement of barb 20 with suture 10, the distance traveled by the respective advancing component(s) may be based on user input taking into account any or all of, the distance between suture 10 and barb 20, the thickness of suture 10 and the length of retaining portion 24 of barb 20. Alternatively, the distance traveled by the respective advancing component(s) may be controlled by one or more sensors included in either or both of suture supply mechanism 110 and barb supply mechanism 130 for sensing a predetermined force between suture 10 and barb 20.

As discussed above, pusher 113 may include a knife or other mechanism (not shown) for separating barb 20 from support posts 144a, 144b. In one embodiment, advancement of pusher 113 relative to barb 20 shears barb 20 from support posts 144a, 144b. Alternatively, pusher assembly 112 may include a heater or ultrasonic mechanism (not shown) for heating or ultrasonically vibrating pusher 113 to facilitate separation of barb 20 from support posts 144a, 144b. As also discussed above, leg members 30, 32 (FIG. 3) of retaining portion 22 may including a coating which may require activation. Thus, prior to engagement of barb 20 with suture 10, the coating on leg members 30, 32 must be activated. Alternatively, activation of the coating may occur after engagement of barb 20 with suture 10.

Figure 14:
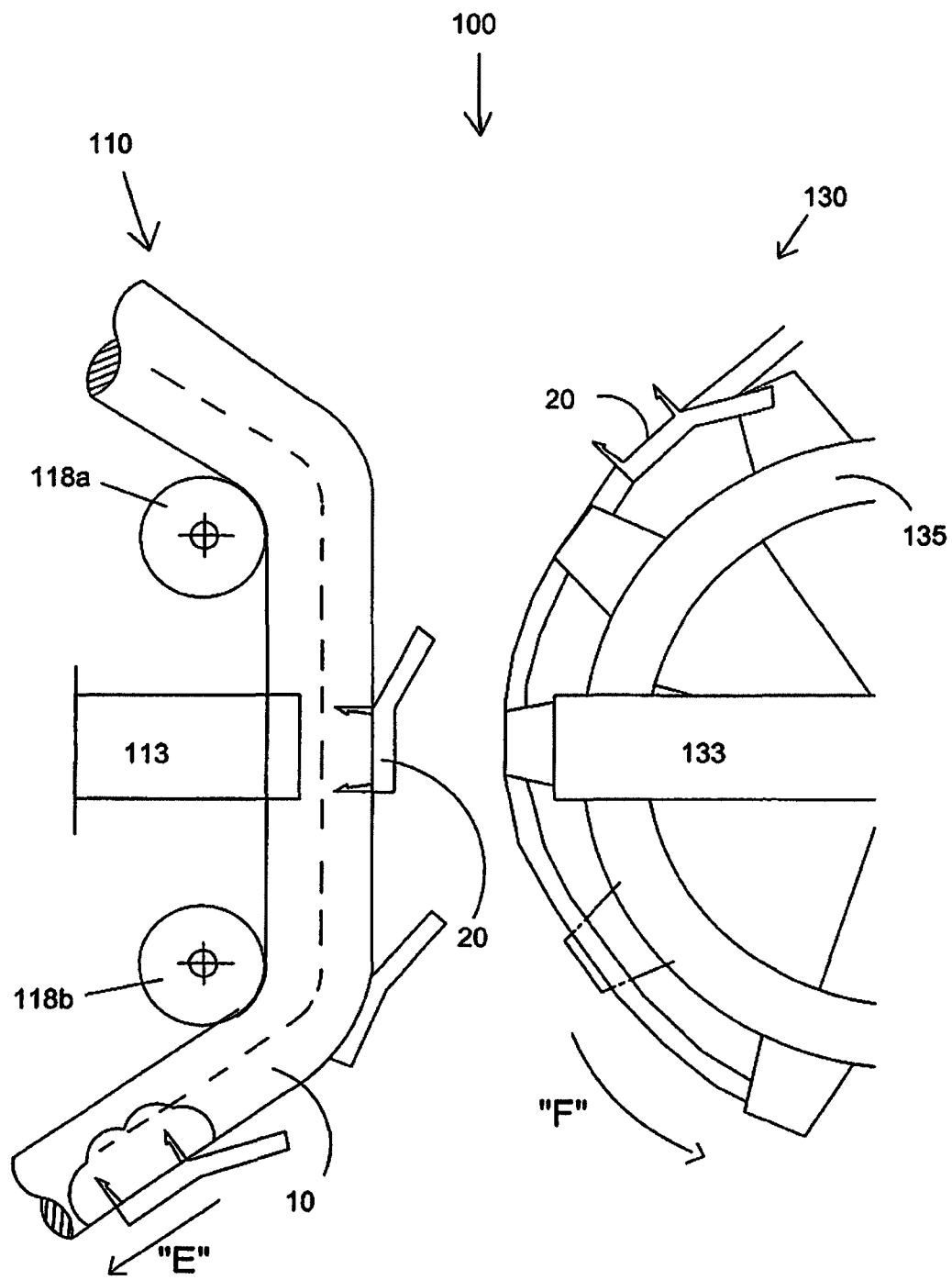
FIG. 14 is the top sectional view of FIG. 12, post affixing of the barb to the suture.

With reference to FIG. 14, following engagement and affixation of barb 20 with suture 10, whichever of the components that was advanced to cause the engagement of barb 20 with suture 10 is retracted to permit subsequent attachment of barbs 20 with suture 10. Suture supply assembly 110 may then be activated to advance suture 10 longitudinally, as indicated by arrow "E", to align a subsequent portion of elongate body 12 with anvil assembly 112. Barb supply assembly 130 may also be activated to advance barb supply assembly 40 longitudinally, as indicated by arrow "F", to align a subsequent barb 20 with pusher assembly 132. The barb fixation process may be repeated as necessary to provide the desired configuration of barbs 20 on suture 10. In one embodiment, suture supply assembly 110 is configured to twist or rotate suture 10 along the length thereof to axially offset subsequently affixed barbs 20.

With reference now to FIGS. 15A and 15B, leg member 230 includes an anchor member 231 according to an alternative embodiment of the present disclosure. As shown, leg member 231 defines a substantially rectangular body. Anchor member 231 includes a leading edge 231a and a pair of trailing edges 231b. Anchor member 231 is configured for more secure engagement with suture 10.

Turning to FIGS. 16A and 16B, leg member 330 includes an anchor member 331 according to another embodiment of the present disclosure. As shown, leg member 331 defines a substantially elliptical body. Anchor member 331 defines a substantially elliptical member having a leading point 331a and a trailing edge 331b extending thereabout.

With reference now to FIGS. 17-19, alternative embodiments of barbs according to the present disclosure are shown generally as barbs 420, 520, 620. Barbs 420, 520, 620 are substantially similar to barb 20 described hereinabove, and will only be described as relates to the differences therebetween. With reference to FIG. 17, barb 420 includes a base portion 422, a retaining portion 424 extending from base portion 422 and a barb portion 426 extending from base 422. Each of leg members 430, 432 extend from base portion 422 and away from each other. Although shown including both leg members 430, 432 extending outward, away from one another, it is envisioned that only one of leg members 430, 432 may extend away from the other leg member 430, 432. Barb portion 426 of barb 420 may include an elongate member 427 having a split or double pointed end 427a configured to more secure engage tissue.

With reference now to FIG. 18, barb 520 includes a retaining portion 524 extending from a base portion 522 and including a pair of leg members 530, 532 extending from base portion 522 and towards each other. Although shown including both leg members 530, 532 extending towards the other, it is envisioned that only one of leg members 530, 532 may extend towards the other leg member 530, 532. Leg members 530, 532 each include a pair of anchor members 531, 533 formed along the length thereof to facilitate securement of barb 520 with suture 10 (FIG. 1A). Barb 520 further includes a barb portion 526. Barb portion 526 includes a tapered elongate member 527. With reference now to FIG. 19, barb 620 includes a base 622, a retaining portion 624 and a barb portion 626. Retaining portion 624 includes three leg members 630, 632, 634 for more securely affixing barb 620 with suture 10 (FIG. 1A).

While the above description contains many specifics embodiments, these embodiments should not be construed as limitations on the scope of the disclosure, but merely as exemplifications of embodiments thereof. Those skilled in the art will envision many other possibilities within the scope and spirit of the disclosure as defined by the claims appended hereto. For example, the barb fixation system may include multiple anvil assemblies and multiple barb supply mechanism for simultaneously affixing multiple barbs to the elongate body of the suture. It is also envisioned that the barbs may be affixed to the suture at an angle relative to the elongate body of the suture rather than, as shown, aligned with the elongate body of the suture.

The invention claimed is:

1. A barbed suture comprising at least one barb, the at least one barb comprising:
   a base portion;
   a retaining portion including a pair of leg members extending parallel to each other from the base portion in a same first direction, each of the pair of leg members including at least one anchor member configured for securing engagement with a suture; and
   a barb portion extending in a second direction from the base portion and configured for engaging tissue, wherein the base portion, the retaining portion, and the barb portion are coplanar when the retaining portion engages the suture and the barb portion is configured for engaging tissue.

2. The barbed suture of claim 1, wherein the at least first anchor member includes one or more barbs or ridges.

3. The barbed suture of claim 1, wherein at least a first leg member of the pair of leg members includes a plurality of anchor members.

4. The barbed suture of claim 3, wherein the plurality of anchor members are spaced along the first leg member.

5. The barbed suture of claim 3, wherein the plurality of anchor members alternate along the first leg member.

6. The barbed suture of claim 1, wherein the barb portion extends beyond an end of the base portion.

7. The barbed suture of claim 6, wherein the base portion, the barb portion, and the retaining portion are integrally formed.

8. The barbed suture of claim 1, wherein the pair of leg members extends from opposed ends of the base portion.

9. A barbed suture comprising:
   an elongate body; and
   at least one barb including a base portion, a retaining portion, and a barb portion, wherein the retaining portion includes a pair of parallel leg members extending in a first direction laterally from the base portion into the elongate body to securely affix the at least one barb to the elongate body, and the barb portion extends in a second direction from the base portion, wherein an end of the base portion and an end of the barb portion are coterminous with each other wherein the barb portion is axially aligned with the base portion.

10. The barbed suture of claim 9, wherein the elongate body comprises a monofilament or a multifilament structure.

11. The barbed suture of claim 9, wherein each leg member of the pair of parallel leg members includes at least a first anchor member.

12. The barbed suture of claim 9, wherein the base portion is tapered.

13. The barbed suture of claim 9, wherein the barb portion extends at an angle with respect to the base portion.

* * * * *